United States Patent
Thorhallsdottir et al.

(10) Patent No.: US 8,128,709 B2
(45) Date of Patent: Mar. 6, 2012

(54) FUNCTIONAL FOOT COVER

(75) Inventors: Hjordis Thorhallsdottir, Reykjavik (IS); Erla Sigridur Gestsdottir, Mosfellsbaer (IS); Arinbjörn Viggo Clausen, Reykjavik (IS); Cristophe Lecomte, Reykjavik (IS); Heidrun Gigja Ragnarsdottir, Reykjavik (IS)

(73) Assignee: Össur hf, Reykjavik (IS)

( * ) Notice: Subject to any disclaimer, the term of this patent is extended or adjusted under 35 U.S.C. 154(b) by 1507 days.

(21) Appl. No.: 11/139,009

(22) Filed: May 26, 2005

(65) Prior Publication Data
US 2006/0015192 A1   Jan. 19, 2006

Related U.S. Application Data

(60) Provisional application No. 60/575,142, filed on May 28, 2004, provisional application No. 60/575,587, filed on May 28, 2004.

(51) Int. Cl.
*A61F 2/66* (2006.01)
(52) U.S. Cl. ............................................ 623/53; 623/55
(58) Field of Classification Search .................... 623/53
See application file for complete search history.

(56) References Cited

U.S. PATENT DOCUMENTS
1,649,773 A   11/1927   Witmyer
(Continued)

FOREIGN PATENT DOCUMENTS
DE   936 161   12/1955
(Continued)

OTHER PUBLICATIONS

Search Report for PCT Application No. PCT/US2005/018737, mailed May 4, 2006.

*Primary Examiner* — Bruce E Snow
*Assistant Examiner* — Melissa Hoban
(74) *Attorney, Agent, or Firm* — Knobbe, Martens, Olson & Bear, LLP

(57) ABSTRACT

A cover for a foot prosthesis comprises an opening at a top end of the cover, which extends into a cavity formed within the cover, wherein the cavity is configured to receive a prosthesis therein. A wall surrounds the cavity and has the shape of a natural human foot. The wall has an inner surface and an outer surface. The wall also has a top section, a bottom section and a rear section. The bottom section defines a sole area having a toe section, a heel section, and a metatarsal region, wherein the sole area is provided with varying levels of stiffness configured to induce a desired rollover from heel-to-toe in a lateral-to-medial direction.

28 Claims, 19 Drawing Sheets

U.S. PATENT DOCUMENTS

| | | | |
|---|---|---|---|
| 3,335,428 A | | 8/1967 | Gajdos |
| 4,652,266 A * | | 3/1987 | Truesdell .................. 623/55 |
| 4,756,098 A * | | 7/1988 | Boggia ....................... 36/114 |
| 4,865,612 A | | 9/1989 | Arbogast et al. |
| 5,156,632 A | | 10/1992 | Wellershaus |
| 5,219,365 A | | 6/1993 | Sabolich |
| 5,443,522 A | | 8/1995 | Hiemisch |
| 5,593,453 A * | | 1/1997 | Ahlert ........................ 623/27 |
| 5,888,239 A | | 3/1999 | Wellershaus et al. |
| 5,897,594 A | | 4/1999 | Martin et al. |
| 5,899,944 A | | 5/1999 | Phillips |
| 6,261,324 B1 | | 7/2001 | Merlette |
| 6,387,134 B1 | | 5/2002 | Parker et al. |
| 6,443,995 B1 | | 9/2002 | Townsend et al. |
| 6,669,737 B2 | | 12/2003 | Mosler et al. |
| 6,718,656 B2 | | 4/2004 | Houser et al. |
| 6,811,571 B1 * | | 11/2004 | Phillips ....................... 623/55 |
| 6,875,240 B1 | | 4/2005 | Laghi |
| 7,181,866 B2 * | | 2/2007 | Braunschweiler .......... 36/28 |
| 7,279,011 B2 | | 10/2007 | Phillips |
| 7,347,877 B2 | | 3/2008 | Clausen et al. |
| 7,618,464 B2 | | 11/2009 | Christensen |
| 7,727,285 B2 | | 6/2010 | Christensen et al. |
| 7,846,213 B2 | | 12/2010 | Lecomte et al. |
| 7,998,221 B2 | | 8/2011 | Lecomte et al. |
| 2002/0038522 A1 * | | 4/2002 | Houser et al. .............. 36/28 |
| 2003/0045944 A1 | | 3/2003 | Mosler et al. |
| 2004/0000074 A1 * | | 1/2004 | Auger et al. ................ 36/102 |
| 2005/0071018 A1 | | 3/2005 | Phillips |
| 2005/0267603 A1 | | 12/2005 | Lecomte et al. |
| 2007/0027557 A1 | | 2/2007 | Jonsson et al. |
| 2009/0287315 A1 | | 11/2009 | Lecomte et al. |
| 2010/0004757 A1 | | 1/2010 | Clausen et al. |

FOREIGN PATENT DOCUMENTS

| | | |
|---|---|---|
| DE | 21 30 168 | 1/1973 |
| DE | 299 12 832 U1 | 7/1999 |
| EP | 1 149 568 A1 | 10/2001 |
| GB | 120462 | 11/1918 |
| WO | WO 02/28326 | 4/2002 |

\* cited by examiner

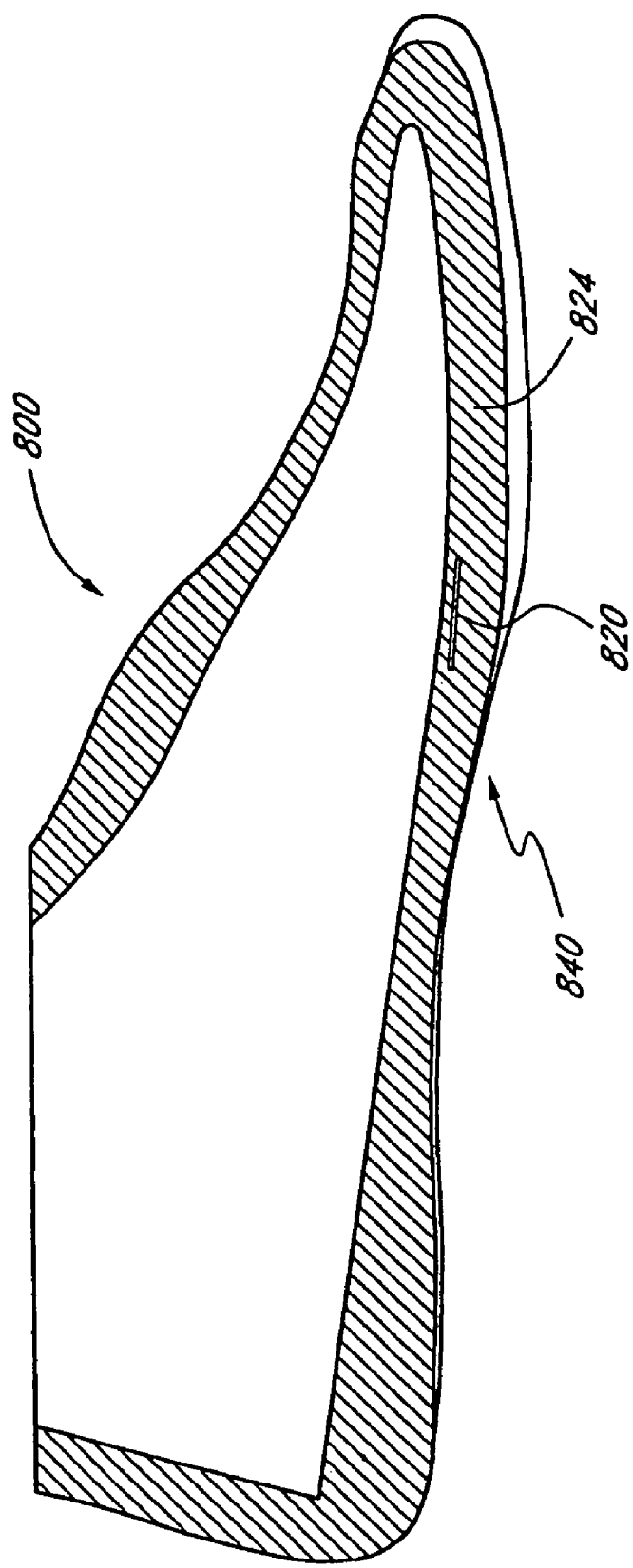

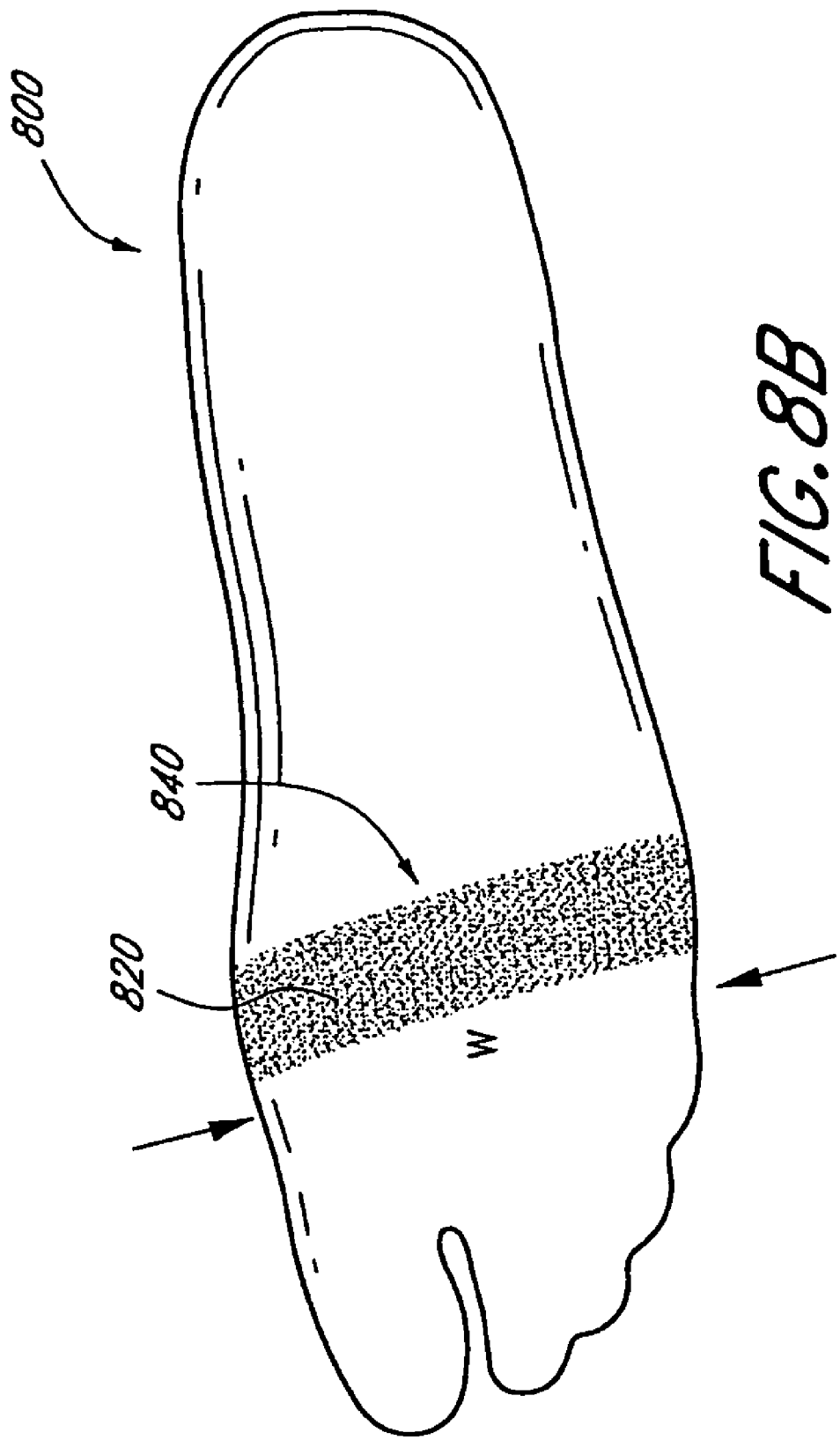

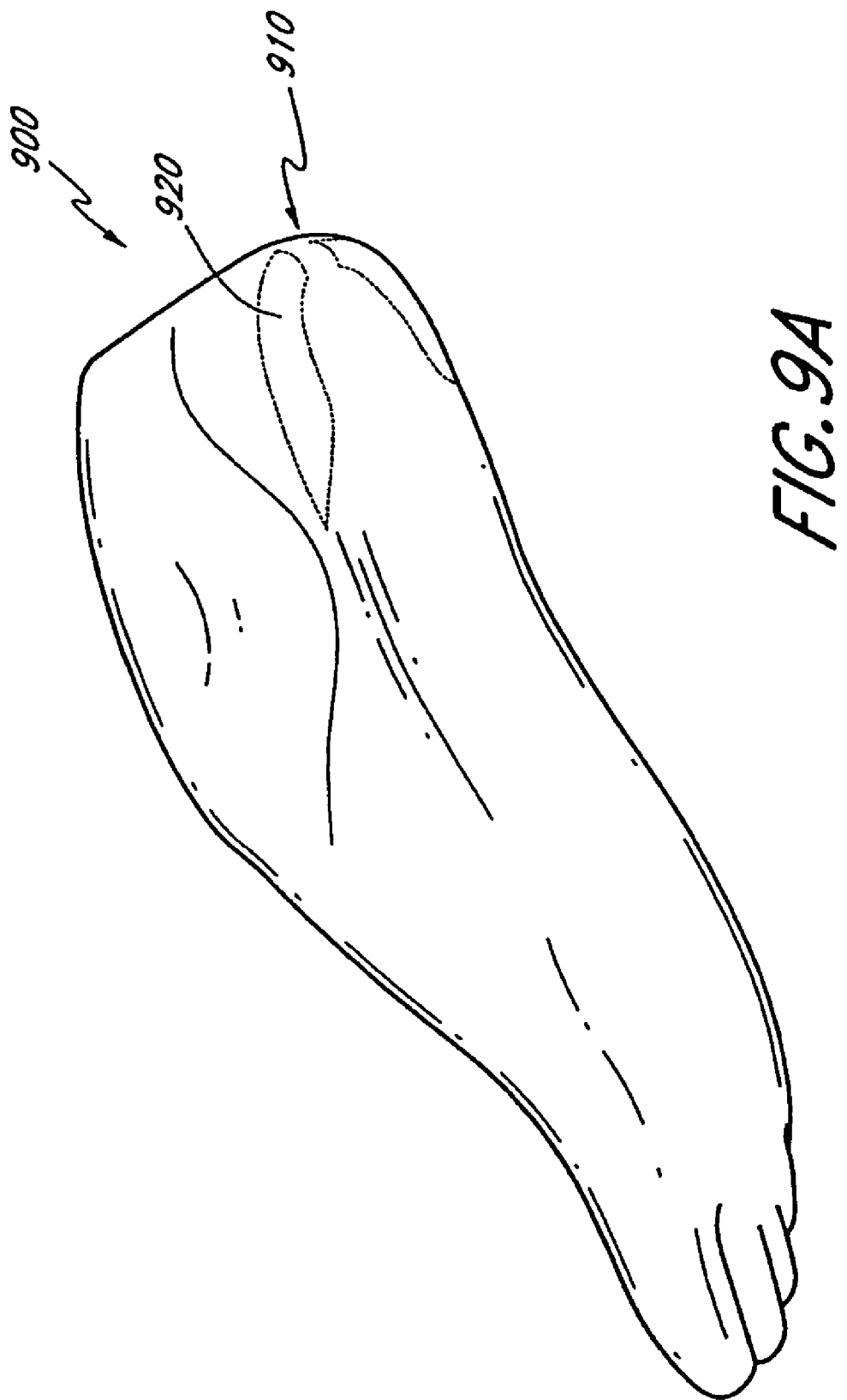

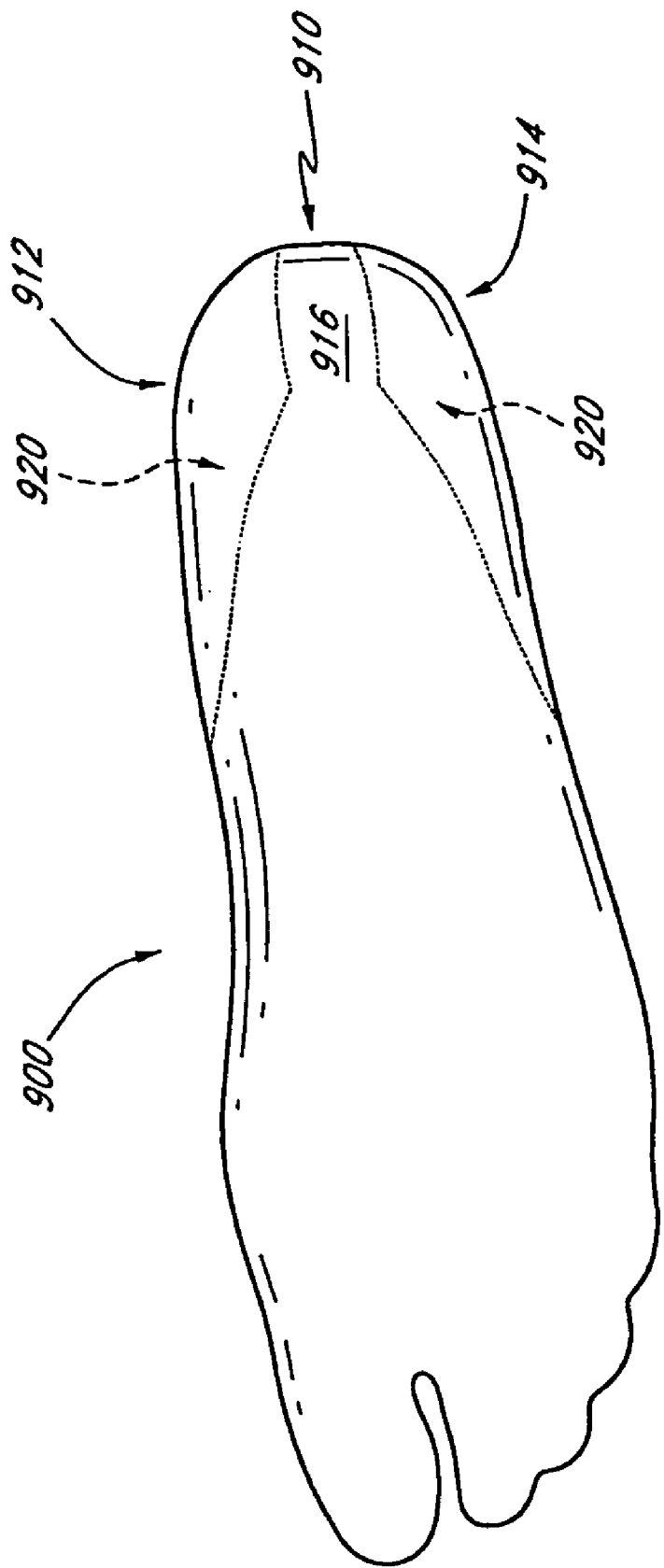

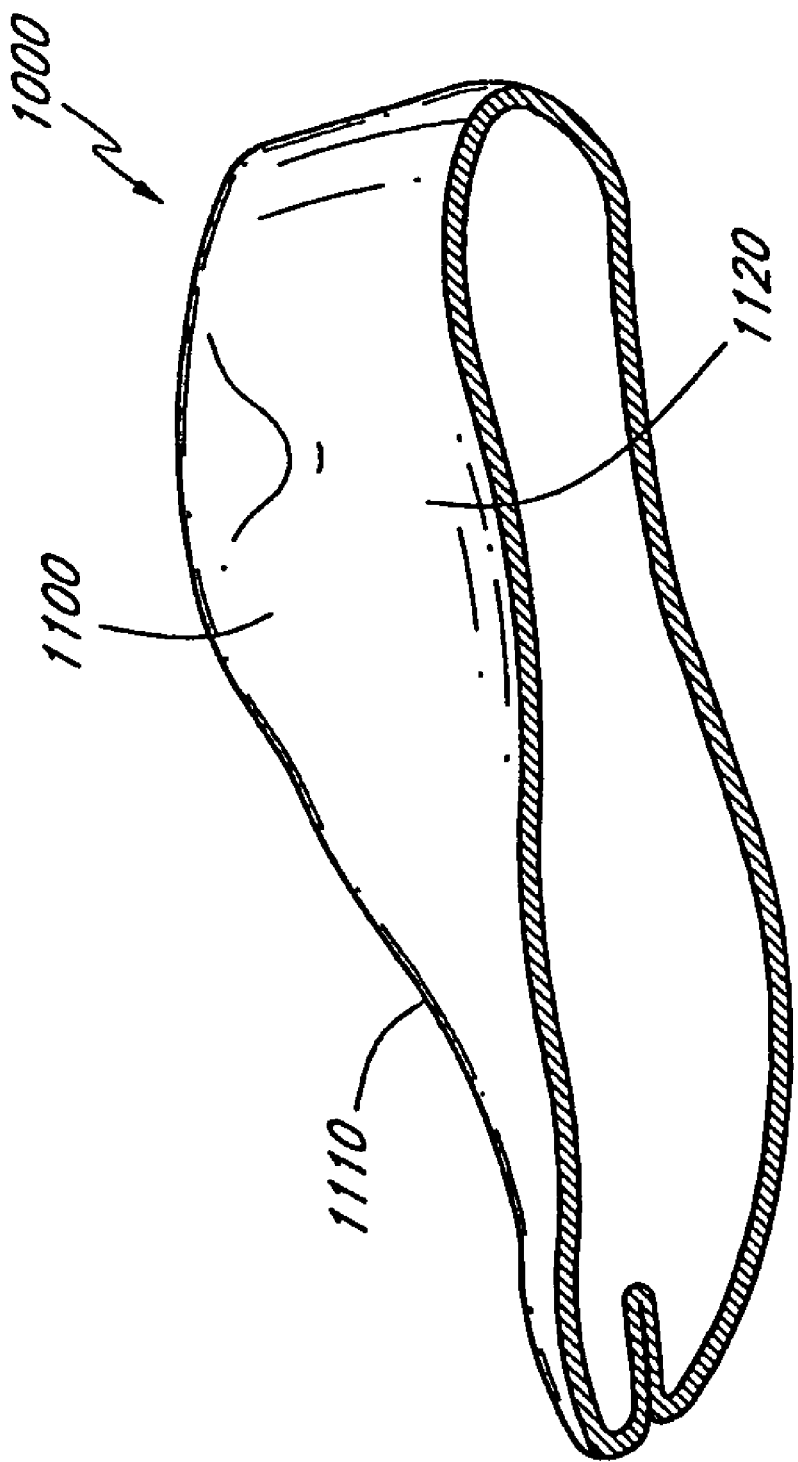

FUNCTIONAL FOOT COVER

CROSS-REFERENCE TO RELATED APPLICATIONS

This application claims priority to U.S. Provisional Patent Applications No. 60/575,142 and No. 60/575,587, both filed May 28, 2004, the entire contents of which are hereby expressly incorporated by reference and should be considered a part of this specification.

BACKGROUND OF THE INVENTION

1. Field of the Invention

The present invention relates to foot covers and, in particular, to covers for a foot prosthesis.

2. Description of the Related Art

Conventional prosthetic foot designs are sometimes enclosed in a cosmesis or cover to improve the aesthetic appeal of the prosthesis, as shown, for example, in U.S. Pat. No. 4,865,612 to Arbogast et al. Some conventional cosmesis designs have the shape of a human foot and are made, for example, of rubber or other flexible materials, which provide additional cushion to the prosthesis during use. However, conventional cosmeses are not designed enhance the performance of the prosthesis based on the nature and impact-level of the expected use.

Accordingly, there is a need for an improved foot cover that can be used in combination with a prosthesis to achieve a desired performance based on the impact-level of the expected use.

SUMMARY OF THE INVENTION

In accordance with one embodiment disclosed herein, a cover for a foot prosthesis is provided. An opening at a top end of the cover extends into a cavity formed within the cover, wherein the cavity is configured to receive a prosthesis therein. A wall surrounds the cavity and has the shape of a natural human foot. The wall has an inner surface and an outer surface. The wall also has a top section, a bottom section and a rear section. The bottom section defines a sole area having a toe section, a heel section, and a metatarsal region, wherein the sole area is provided with varying levels of stiffness configured to induce a desired rollover from heel-to-toe, a portion of the desired rollover being in a lateral-to-medial direction.

In accordance with another embodiment disclosed herein, a cover for a foot prosthesis is provided comprising an opening at a top end of the cover. The opening extends into a cavity within the cover configured to receive a prosthesis therein. A wall surrounds the cavity and has the shape of a natural human foot. The wall has an inner surface and an outer surface. The wall also has a top section, a bottom section and a rear section. The bottom section defines a sole area having a toe section, a heel section, and a metatarsal region, wherein the sole area is provided with a plurality of selected regions of differing stiffness relative to areas surrounding said selected regions.

In accordance with still another embodiment disclosed herein, a cover for a foot prosthesis is provided comprising an opening at a top end of the cover. The opening extends into a cavity within the cover configured to receive a prosthesis therein. A wall surrounds the cavity and has the shape of a natural human foot. The wall has an inner surface and an outer surface. The wall also has a top section, a bottom section and a rear section. The bottom section defines a sole area having a toe section, a heel section, and a metatarsal region, wherein the sole area is provided with at least one selected region of reduced stiffness relative to an area surrounding said selected region.

In accordance with yet another embodiment disclosed herein, a cover for a foot prosthesis is provided, the cover having the shape of a natural human foot. An opening at a top end of the cover extends into a cavity within the cover, the cavity configured to receive a prosthesis therein. A top section extends between the opening and a toe section. A rear section extends between the opening and a heel section. A bottom section defines a sole area between the heel section and the toe section, the sole area having a metatarsal region extending between an inner edge and an outer edge of the bottom section. A section of shock absorbing material is disposed on the sole area and has a first selected stiffness. The section of shock absorbing material is configured to provide a desired level of shock absorption. A section of energy return material is disposed on the sole area and has a second selected stiffness. The section of energy return material is configured to provide a desired level of energy return. The sections of shock absorbing material and energy return material effect a desired rollover during a transition from heel-strike to toe-off to approximate the rollover of a human foot.

In accordance with another embodiment disclosed herein, a cover for a foot prosthesis is provided, wherein the cover has the shape of a natural human foot. The cover comprises a bottom section that defines a heel section, a toe section, and a metatarsal region therebetween. A first material is disposed on the heel section and has a first selected stiffness. A second material is disposed on the metatarsal section and has a second selected stiffness different from the first selected stiffness, wherein the first and second materials induce a rollover during a transition from heel-strike to toe-off, a portion of the desired rollover being in a lateral-to-medial direction.

BRIEF DESCRIPTION OF THE DRAWINGS

FIG. 8A is a cross-sectional side view of another embodiment of a functional foot cover.

FIG. 8B is a bottom plan view of the functional foot cover in FIG. 8A.

FIG. 9A is a bottom, side and rear profile view of another embodiment of a functional foot cover.

FIG. 9B is a bottom plan view of the functional foot cover in FIG. 9A.

FIG. 10B is a bottom, side and rear profile view of the functional foot cover in FIG. 10A.

DETAILED DESCRIPTION OF THE PREFERRED EMBODIMENTS

Foot covers are known in the art and are described, for example, in pending U.S. application Ser. No. 09/586,666, filed Jun. 1, 2000, the contents of which are incorporated herein by reference in their entirety.

Figure 1:
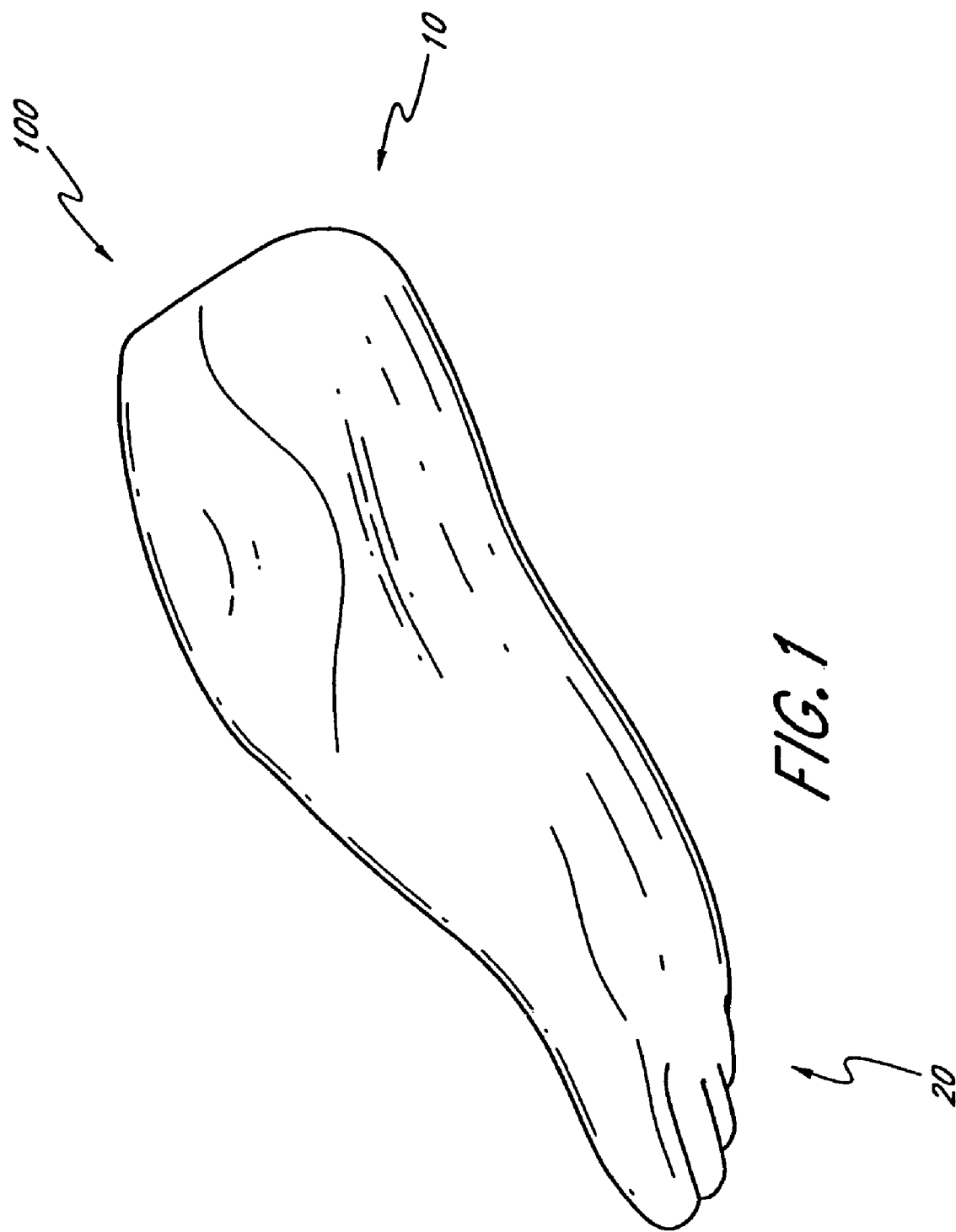
FIG. 1 is a bottom and side profile view of one embodiment of a functional foot cover.

FIG. 1 illustrates one embodiment of a functional foot cover 100. Preferably, the functional foot cover 100 has the shape of a natural human foot, including a heel section 10 and a toe section 20. In one preferred embodiment, the functional foot cover 100 can be made of polyurethane or a similar material. However, the functional foot cover 100 can be made of other suitable materials, such as materials commonly used for the manufacture of prosthetic cosmeses.

Figure 2A:
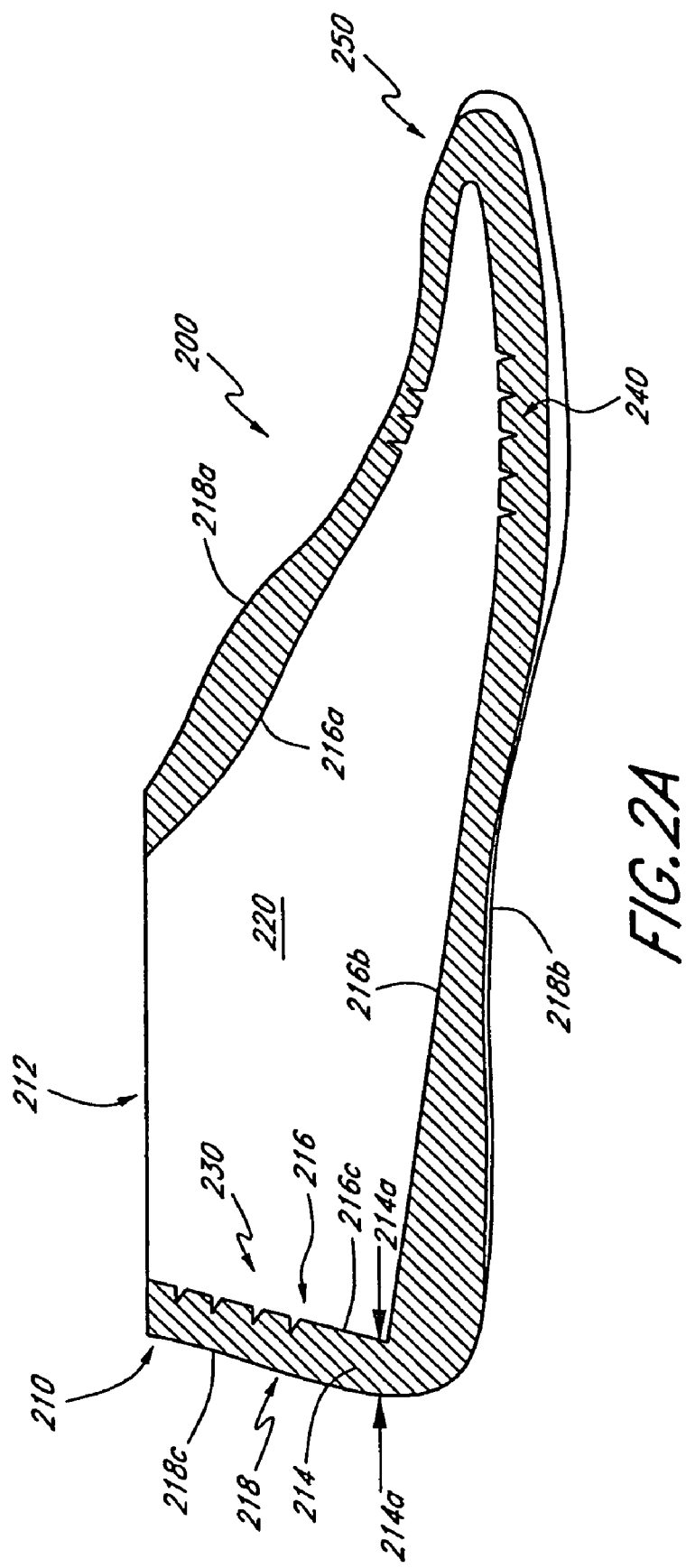
FIG. 2A is a cross-sectional side view of the functional foot cover in FIG. 1.
Figure 2B:
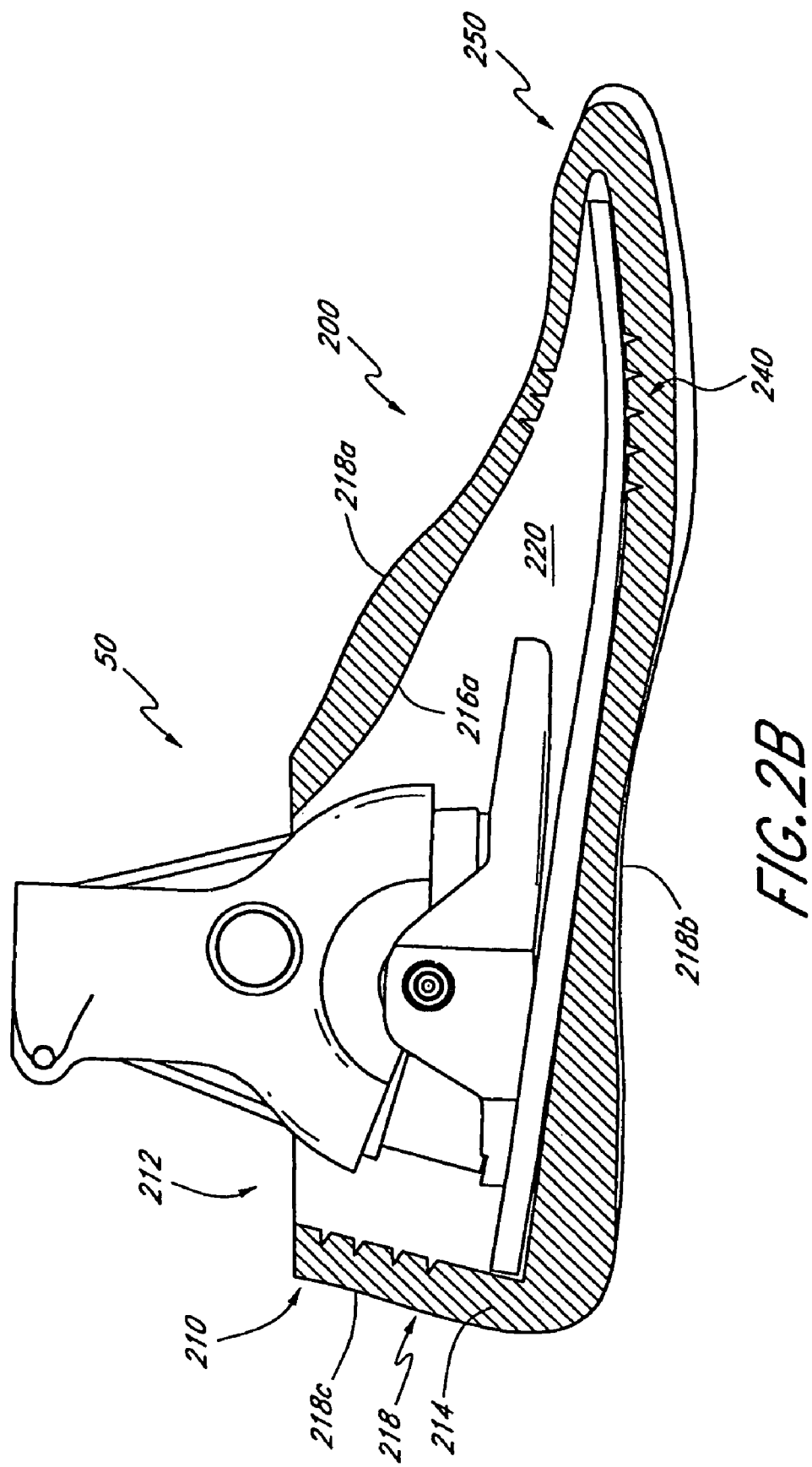
FIG. 2B is a side view of a prosthetic foot in combination with the functional foot cover of FIG. 2A.

FIG. 2A illustrates a cross-section of another embodiment of a functional foot cover 200. The functional foot cover 200 is preferably configured to receive a prosthesis therein, such as the prosthetic foot 50 illustrated in FIG. 2B. In the illustrated embodiment, the prosthetic foot 50 is an Elation™ Foot by Össur of Reykyavik, Iceland. However, the use of any of the functional foot cover embodiments disclosed herein is contemplated with any prosthetic foot design.

In the illustrated embodiment, the foot cover 200 has an opening 212 at a top end 210 thereof and a wall 214 having an inner surface 216 and an outer surface 218. The inner surface 216 comprises a top section 216a, a bottom section 216b and a rear section 216c Likewise, the outer surface 218 comprises a top section 218a, a bottom section 218b and a rear section 218c. The opening 212 and inner surface 216 together define a cavity 220 within the functional foot cover 200. Preferably, at least one recess 230 is formed on the inner surface 216 of the wall 214. In the illustrated embodiment, a plurality of recesses 230 are shown, some of which are disposed on the bottom section 216b along a metatarsal region 240 proximal a toe section 250 of the foot cover 200. Recesses 230 can also be disposed on the rear 216c and top 216a sections of the wall 214. In another embodiment, the recesses 230 can be formed on the outer surface 218 of the foot cover 200. Preferably, the recesses 230 are disposed on the foot cover 200 so as to facilitate flexion of the foot cover 200 during use. For example, when the foot cover 200 is placed on a prosthetic foot, the recesses 230 facilitate the flexion of the cover 200 during the prosthetic foot's walking motion, such as during toe-off. Accordingly, the recesses 230 advantageously provide a functional foot cover 200 with improved rollover characteristics. In one embodiment, the recesses 230 are notches 230 formed on the inner surface 216 of the wall 214 of the functional foot cover 200, as illustrated in FIG. 2. In a preferred embodiment, the notches 230 extend between about ¼ and about ½ of a thickness 214a of the wall 214 of the foot cover 200. However, the notches 230 can have other depths, such as less than about ¼ of the thickness 214a of the wall 214, or more than about ½ of the thickness 214a of the wall 214, as desired.

Figure 3:
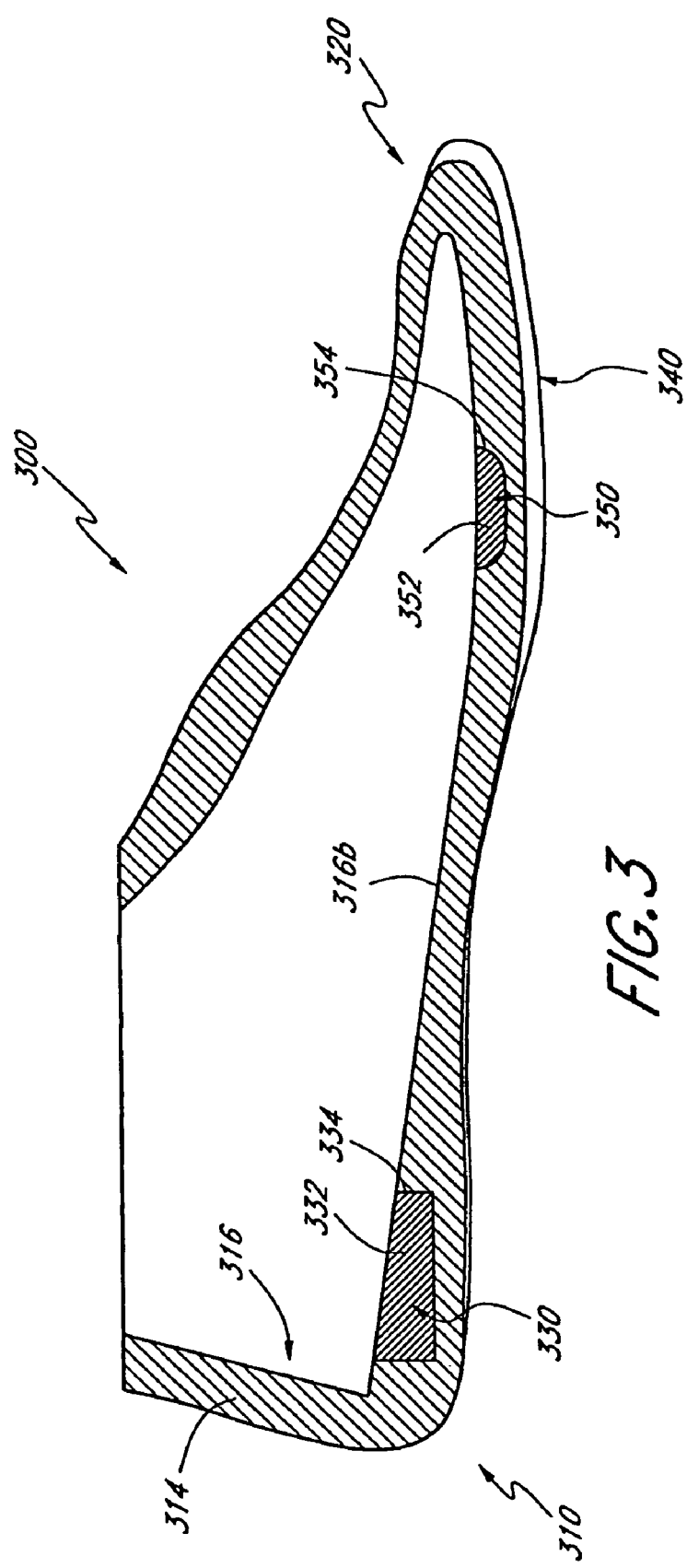
FIG. 3 is a cross-sectional side view of another embodiment of a functional foot cover.

FIG. 3 illustrates a cross-sectional side view of another embodiment of a functional foot cover 300. In the illustrated embodiment, a shock absorbing material 330 is preferably disposed in the heel section 310 of the foot cover 300. For example, the shock absorbing material 330 can be inserts 332 disposed in cavities 334 formed on the inner surface 316 of the foot cover 300. Preferably, the shock absorbing material 330 can be embedded into the heel section 310. In another embodiment, the shock absorbing material 330 can be attached to the inner surface 316 of the foot cover 300 with, for example, an adhesive. In still another embodiment, the shock absorbing material 330 can be removably attached to the inner surface 316 of the foot cover 300. For example, the shock absorbing material 330 can comprise inserts 332 that lockingly engage recesses or cavities (not shown) formed on the inner surface 316 of the foot cover 300. As shown in FIG. 3, the shock absorbing material 330 is disposed on at least a portion of the heel section 310. In a preferred embodiment, the shock absorbing material 330 covers an area between about 6 cm$^2$ and about 20 cm$^2$ of the heel section 310. In other embodiments, the shock absorbing material 330 can cover an area of less than about 6 cm$^2$. In still other embodiments, the shock absorbing material 330 can cover an area of more than about 20 cm$^2$.

The shock absorbing material 330 is preferably disposed on areas of the foot cover 300 that receive high impact forces during use. In one embodiment, the shock absorbing material 330 is EVA, or a similar material. However, other materials providing suitable shock absorbing characteristics can also be used.

As illustrated in FIG. 3, an energy return material 350 is also disposed in the metatarsal area 340 proximal the toe section 320 of the foot cover 300. In one embodiment, the energy return material 350 can comprise inserts 352 disposed in cavities 354 formed on the inner surface 316 of the foot cover 300. Preferably, the energy return material 350 is embedded into the wall 314 of the foot cover 300. In another embodiment, the energy return material 350 can be attached to the inner surface 316 of the foot cover 300 with, for example, an adhesive. In still another embodiment, the energy return material 350 is removably attached to the inner surface 316 of the foot cover 300. In a preferred embodiment, the energy return material 350 covers at least a portion of the metatarsal region 340 of the foot cover 300. For example, the energy return material 350 can comprise inserts 352 that lockingly engage recesses or cavities 354 formed on the inner surface 316 of the foot cover 300. Preferably, the energy return material 350 covers an area of between about 6 cm$^2$ and about 20 cm$^2$ of the metatarsal region 340 of the foot cover 300. In other embodiments, the energy return material 350 can cover areas less than about 6 cm$^2$. In still other embodiments, the energy return material 350 can cover an area of more than about 20 cm$^2$. Additionally, the energy return material 350 is an elastic material, such as silicone. However, other materials that provide suitable energy return characteristics can also be used.

Figure 4:
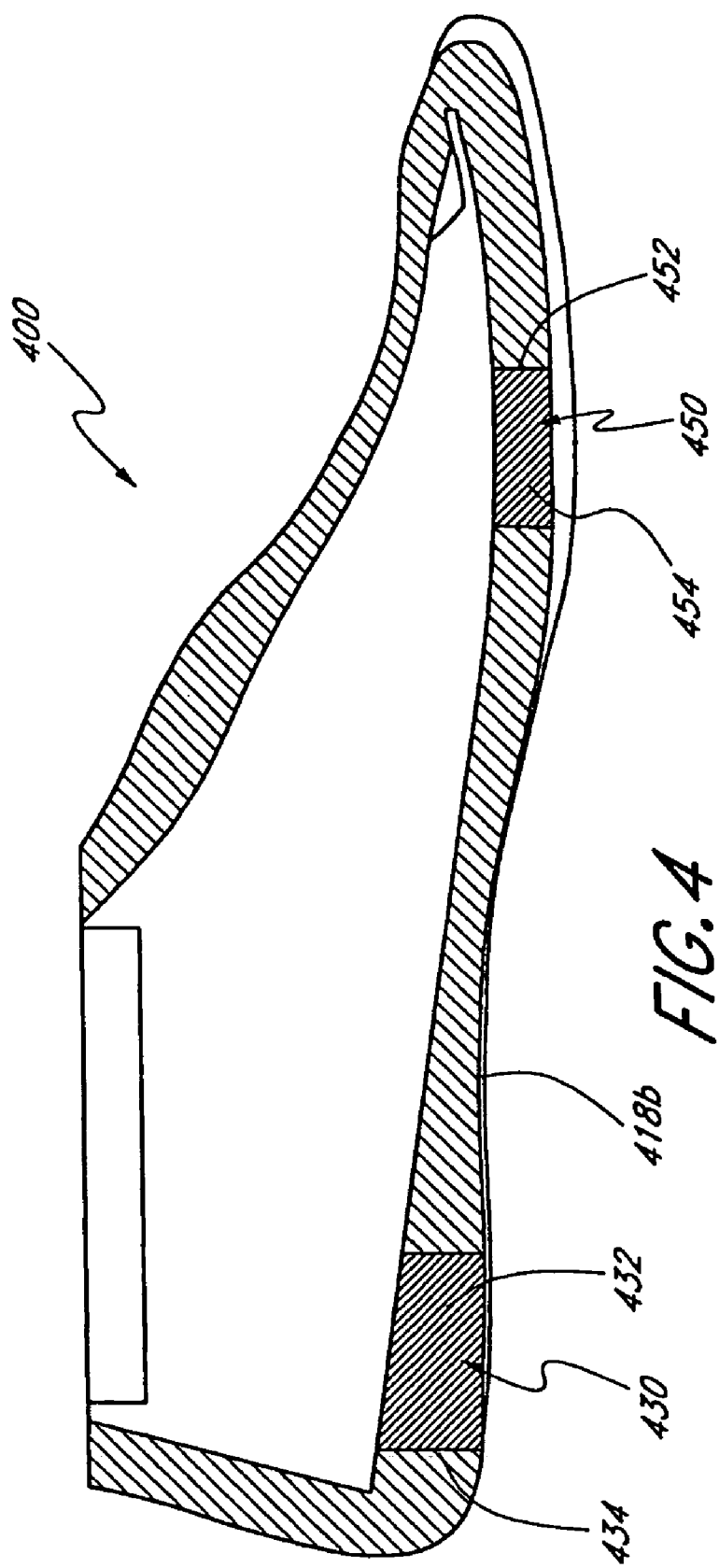
FIG. 4 is a cross-sectional side view of another embodiment of a functional foot cover.

FIG. 4 illustrates another embodiment of a functional foot cover 400. In the illustrated embodiment, the shock absorbing 430 and energy return 450 materials discussed above are attached to a bottom outside surface 418b of the foot cover 400. In one embodiment, the shock absorbing material 430 and energy return material 450 comprise inserts 432, 452 removably disposed in cavities 434, 454 formed on the bottom surface of the foot cover 400, respectively. For example, the shock absorbing 430 and energy return 450 materials can be attached to the foot cover 400 with an adhesive. In another embodiment, the inserts 432, 452 can have engagement members (not shown) that snap onto the recesses or cavities 434, 454. However, the shock absorbing 430 and energy return 450 materials can be attached to the foot cover 400 using other known mechanisms, such as bolts and screws. In another embodiment, the shock absorbing 430 and energy return 450 materials can be molded onto the foot cover 400 during manufacture.

In a preferred embodiment, a set of shock absorbing inserts 432 having varying levels of shock absorption are provided. Accordingly the foot cover 400 can be tailored to provide the level of shock absorption best suited for a particular user's needs. Similarly, a set of energy return inserts 452 with varying levels of energy return can be provided to provide the level of energy return required by a specific user. Accordingly, the shock absorption 430 and energy return 450 materials can be tailored to the particular activity level of the user. For example, for a low-activity user, the shock absorption material 430 can be a highly elastic material, such as a highly elastic urethane or other polymer material. Similarly, for a high activity user, the shock absorption material 430 can be one with a lower elasticity.

Figure 5:
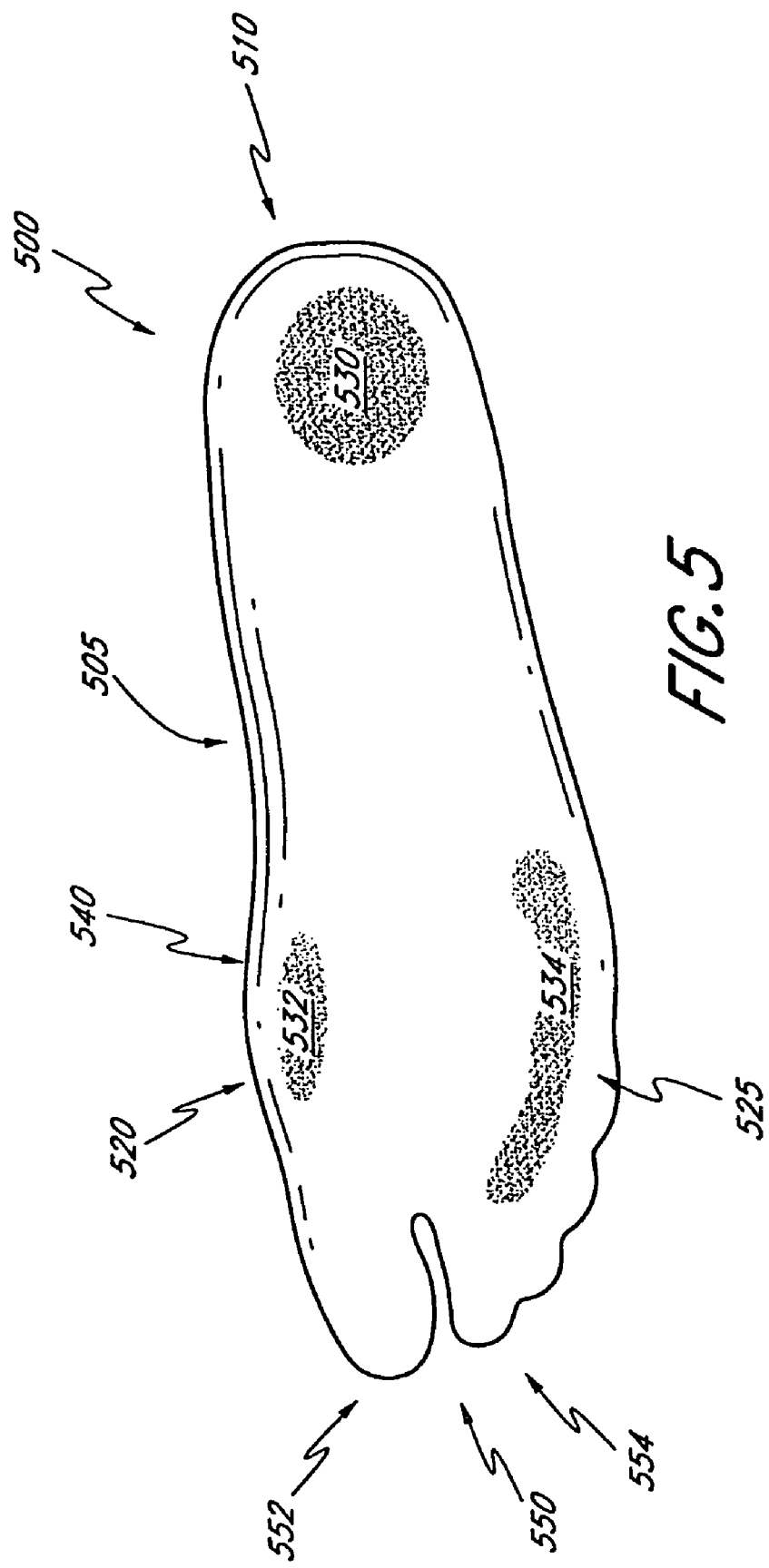
FIG. 5 is a bottom plan view of another embodiment of a functional foot cover.

FIG. 5 illustrates another embodiment of a functional foot cover 500. In the illustrated embodiment, the foot cover 500 comprises materials of selected stiffness disposed along the sole area 505 of the foot cover 500. For example, said materials can have a durometer of between about 60 Shore A and about 95 Shore A. However, in other embodiments, the materials can have other levels of stiffness. In the illustrated embodiment, said materials are injection molded onto the foot cover 500 during manufacture. As shown in FIG. 5, the heel section 510 comprises a first material 530 of selected stiffness. Additionally, at least a portion of the metatarsal region 520 comprises a second material 532 of selected stiffness, which can have the same stiffness as the material in the heel section 510. Still another section 525 of the sole 505 of the foot cover 500 comprises a third material 534 of selected stiffness, which may be different than that of the heel 510 or metatarsal sections 520. It will be obvious to one of ordinary skill in the art that various materials, each having a different stiffness, can be incorporated into the foot cover 500. Moreover, though the illustrated embodiment illustrates three different areas comprising materials of selected stiffness, it will be obvious to one of ordinary skill in the art that more or fewer areas of selected stiffness can be incorporated into the foot cover 500.

Preferably, said materials 530, 532, 534 are disposed, and their stiffness selected, so as to guide the rollover of the foot cover 500 during use. For example, material having a higher stiffness can be disposed on the heel section 510 and be surrounded by material of lower stiffness. In another embodiment, the material disposed on the heel section 510 of the foot cover 500 can have a lower stiffness than the material surrounding said heel section 510. Similarly, the material disposed on the metatarsal region 520 can be disposed, and its stiffness selected, so as to guide the rollover of the foot cover 500. In one embodiment, the material disposed on the metatarsal region 520 has a higher stiffness than the material surrounding said region. In another embodiment, the material disposed on the metatarsal region 520 has a lower stiffness than the surrounding material. In a preferred embodiment, the materials are disposed, and their stiffness selected, so that the functional foot cover 500 rolls over medially toward an inner edge 540 of the foot cover 500 during transition from heel-strike to toe-off and approximates the rollover of a natural human foot.

Preferably, the coverage area of each material of selected stiffness is chosen to adequately guide the rollover of the foot cover 500, as described above. For example, the material disposed on the heel section 510 can have an area of between about 6 cm$^2$ and about 20 cm$^2$. Similarly, the material of selected stiffness disposed on the metatarsal region 520 can have an area of between about 6 cm$^2$ and about 20 cm$^2$. However, in other embodiments the material of selected stiffness can be have an area less or greater than that disclosed above.

Figure 6:
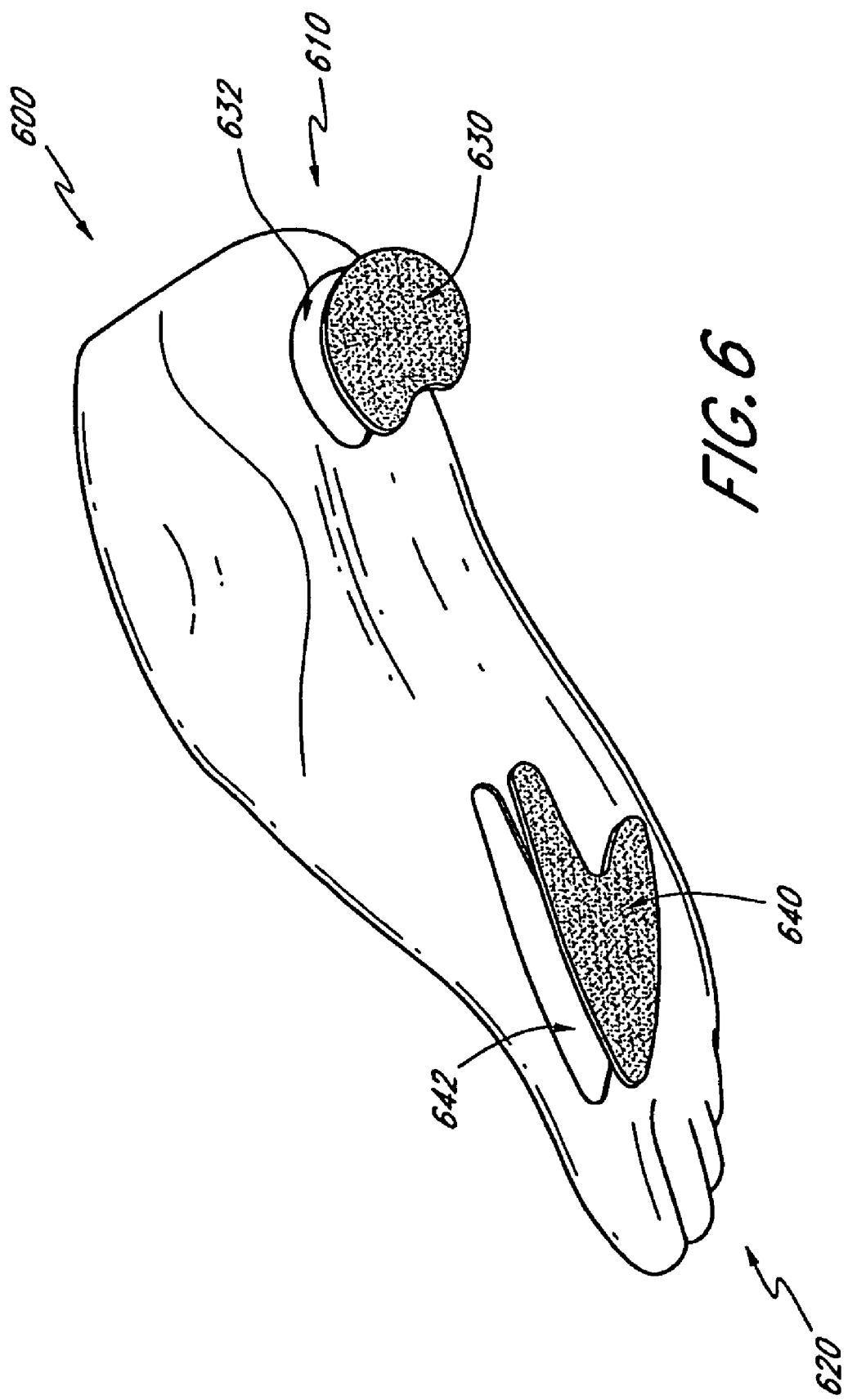
FIG. 6 is a bottom and side profile view of another embodiment of a functional foot cover.

FIG. 6 illustrates another embodiment of a functional foot cover 600. In the illustrated embodiment, the foot cover 600 includes a heel section insert 630 attached thereto and made of a material having a selected stiffness, which preferably differs from the stiffness of the surrounding area on the foot cover 600. Similarly, the foot cover 600 includes a toe section insert 640 attached thereto and made of a material having a selected stiffness, which preferably differs from the stiffness of the surrounding area. Said materials preferably have a durometer of between about 60 Shore A and about 95 Shore A. In other embodiment, said materials can have other levels of stiffness. For example, the materials can have durometers lower or greater than the values noted above. Preferably, the heel and toe section inserts 630, 640 are removably attached to the foot cover 600. For example, the section inserts 630, 640 can be lockingly snapped onto cavities 632, 642 formed on the foot cover 600. In another embodiment, the toe and heel section inserts 630, 640 can be attached to the foot cover 600 with an adhesive. However, the section inserts 630, 640 can be attached to the foot cover 600 using other fixation mechanisms, such as bolts and screws. Preferably, sets of inserts are provided, each having a different stiffness level. Accordingly, the foot cover 600 can be tailored to have a particular rollover characteristic based on the stiffness level of the toe and heel section inserts 630, 640 that are attached to the toe section 620 and heel section 610, respectively, of the foot cover. Moreover, as discussed above, the inserts 630, 640 can be tailored to the particular activity level of the user.

Figure 7:
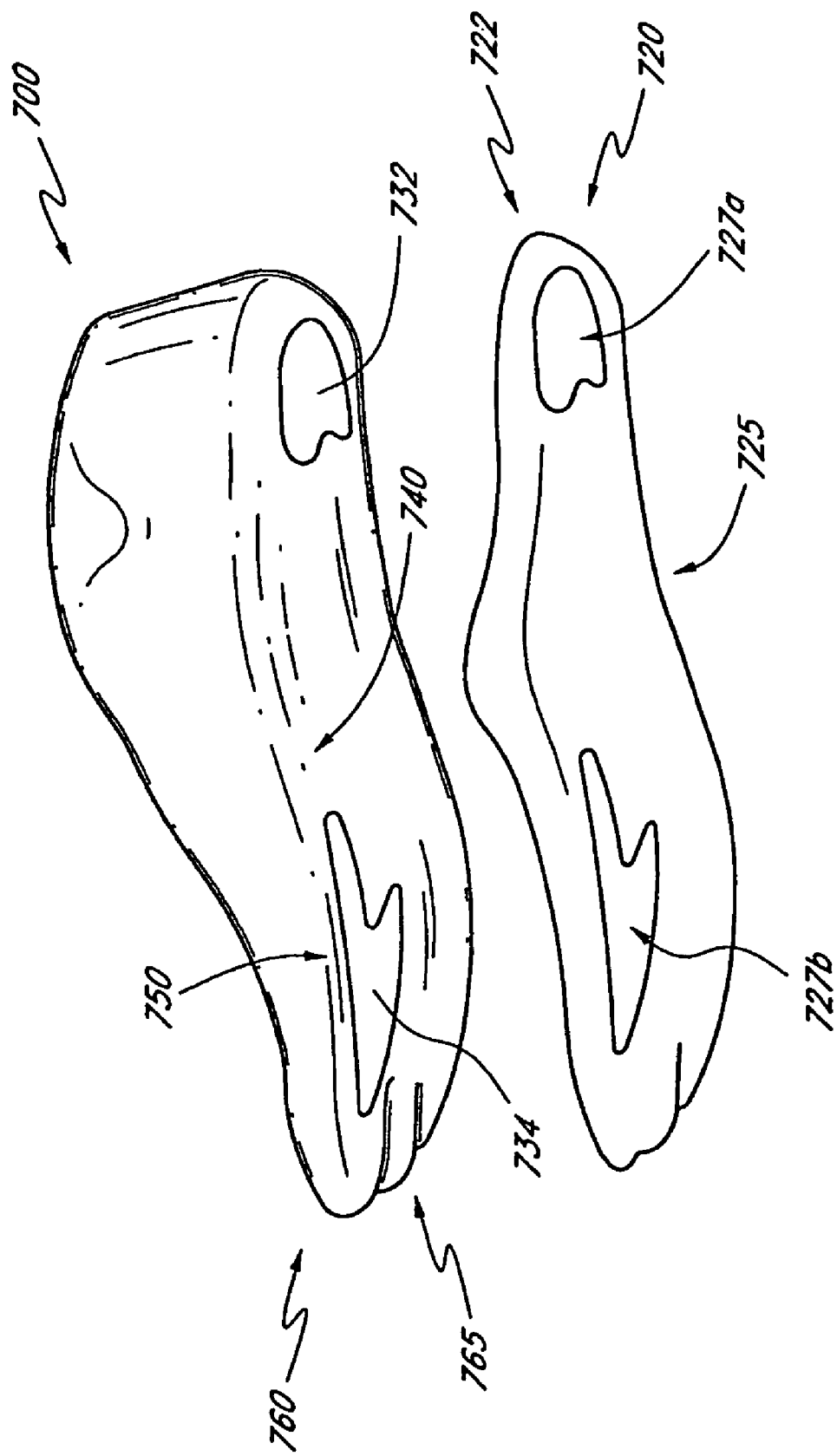
FIG. 7 is a bottom and side profile view of another embodiment of a functional foot cover.

FIG. 7 illustrates another embodiment of a functional foot cover 700. In the illustrated embodiment, a sole portion 720 extending between a heel section 722 and a toe section 724, and defining a metatarsal region 726 therebetween, is provided for attachment to the foot cover 700. The sole portion 720 has areas 725 of selected stiffness with a durometer preferably between about 60 Shore A and about 95 Shore A. In other embodiments, said areas 725 can have a durometer higher than about 95 Shore A. In still other embodiments, said areas 725 can have a durometer lower than about 60 Shore A. In the illustrated embodiment, the sole portion 720 has an opening 727$a$ disposed generally at the heel section 722 and a second opening 727$b$ disposed generally at the metatarsal region 726. The openings 727$a$, 727$b$ are preferably configured to fit over inserts of selected stiffness 732, 734 located generally at a heel section and metatarsal region of the foot cover 700, respectively. In one embodiment, the inserts 732, 734 have a stiffness level different than the stiffness of the surrounding area 725 on the sole portion 720. One of ordinary skill in the art will recognize that the sole portion 720 can have any number of openings configured to accommodate an equal number of inserts of selected stiffness disposed in the foot cover 700. In another embodiment, the sole portion 720 does not have any openings.

In one embodiment, the sole portion 720 is removably attached to the foot cover 700. For example, the sole portion 720 can have members (not shown) that protrude into recesses or cavities (not shown) formed on the bottom of the foot cover 700 so as to lockingly engage the sole portion 720 to the foot cover 700. In another embodiment, the sole portion 720 can be attached to the foot cover 700 with an adhesive. As with the embodiments illustrated in FIGS. 5 and 6, the sole portion 700 can be manufactured using materials of different stiffness to guide the rollover of the foot cover 700 during use.

In a preferred embodiment, said guided rollover is used to control pronation of the foot cover 700 during use. More preferably, the guided rollover approximates the walking motion of a natural human foot, so that the foot cover 700 rolls over medially toward the inner edge 740 of the foot cover 700 during transition from heel-strike and toe-off. One of ordinary skill in the art will recognize that the guided rollover characteristics described above can be incorporated into the sole portion 720 of a cosmesis as described above, as well as an individual sole attached to a prosthetic foot, as described in U.S. Provisional Application No. 60/575,142, filed May 28, 2004, which is incorporated herein by reference in its entirety.

The foot cover 700 preferably comprises a metatarsal region 750 generally parallel to a supporting surface on which the foot cover 700 rests. Additionally, the toe section 760 of the foot cover 700 preferably comprises a set of toes 765 having an upper bend or tilt to provide a smoother toe push-off during use.

FIG. 8A illustrates another embodiment of a functional foot cover 800 with a support member 820 disposed therein. In the illustrated embodiment, the support member 820 is a plate that is preferably embedded in the wall 824 of the foot cover 800. The support member 820 is preferably made of a stiff material. For example, the support member 820 can be made of a carbon fiber material. However, the support member 820 can be made of other suitable materials that provide the desired stiffness, such as a hard plastic. Advantageously, the support member 820 improves the stability of the foot cover 800 along the metatarsal region 840. In one embodiment, the support member 820 extends along a portion of the metatarsal region 840. In another preferred embodiment, the support member 820 attaches to the bottom of the foot cover 800 and extends transversely across substantially the entire width W of the foot cover 800 at the metatarsal region 840, as illustrated in FIG. 8B. In other embodiments, the support member 820 can have other shapes, such as cylindrical. Additionally, the support member 820 can be disposed on other areas of the foot cover 800 requiring additional stability.

FIGS. 9A and 9B illustrate another embodiment of a functional foot cover 900. In the illustrated embodiment, the foot cover 900 includes a heel section 910 having a material of a selected stiffness 920. Preferably, said material of selected stiffness 920 is disposed on the heel section 910 of the foot cover 900 so as to improve the stability of the foot during heel strike. In the illustrated embodiment, the material of selected stiffness 920 is embedded into the heel section 910 so that the medial 912 and lateral 914 edges of the heel are stiffer than the middle portion 916 of the heel. Preferably, said material of selected stiffness 920 is injection molded into the heel section 910 during manufacture of the foot cover 900. In another embodiment, said materials of selected stiffness 920 can be removably attached to the heel section, via for example, snap-on inserts, as discussed above.

Figure 10A:
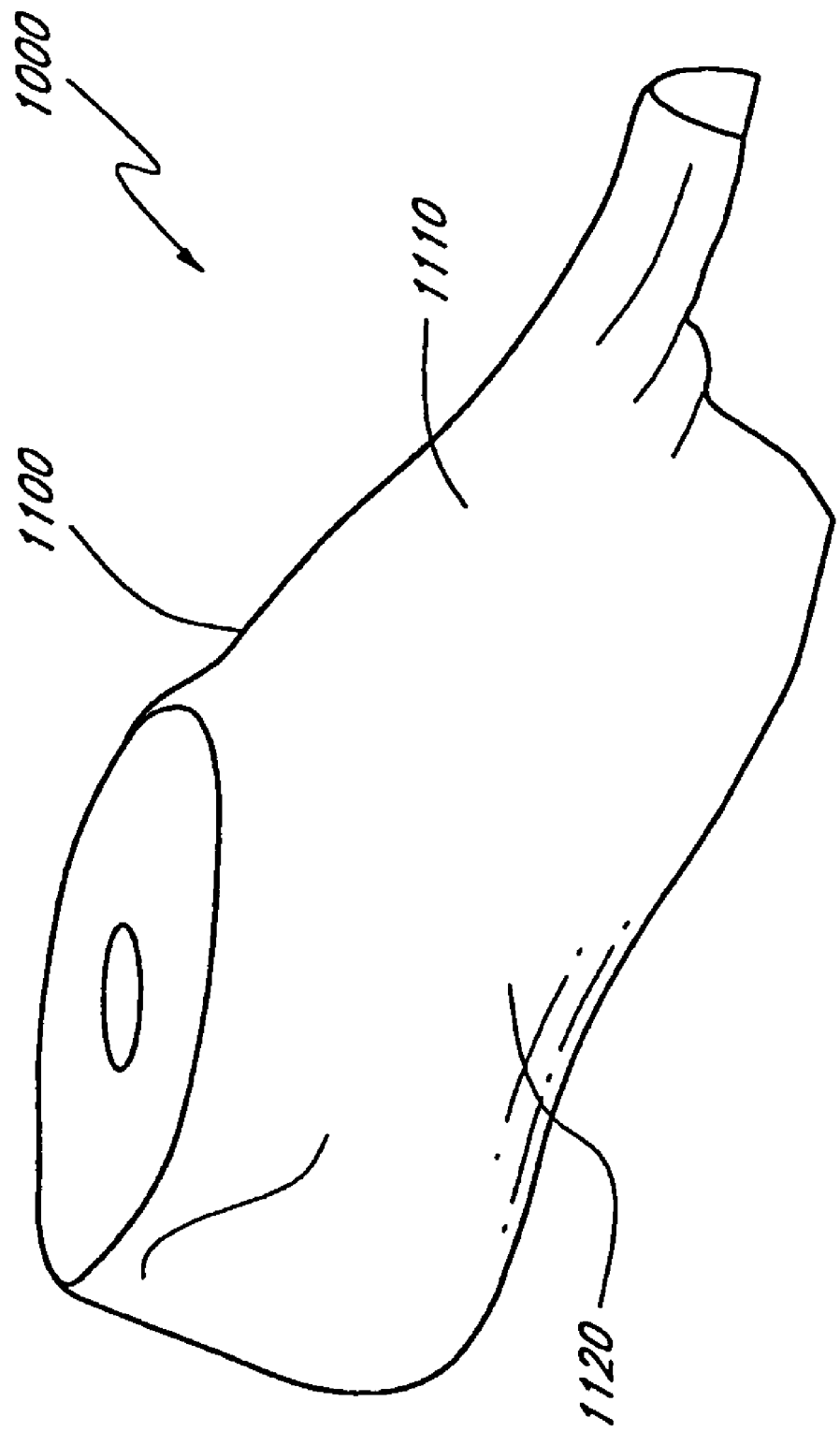
FIG. 10A is a front, top and side profile view of another embodiment of a functional foot cover.

FIGS. 10A and 10B illustrate another embodiment of a functional foot cover 1000. In the illustrated embodiment, the foot cover 1000 comprises the shell 1100 configured to fit over a prosthetic foot or other prosthetic device. In one preferred embodiment, the shell 1100 is sized to fit within conventional footwear, such as a shoe. More preferably, the shell 1100 is sized to substantially completely fill the inside of a shoe. As illustrated in FIG. 10B, the shell 1100 comprises a top surface 1110 and a side surface 1120, but does not have a bottom surface.

Figure 11A:
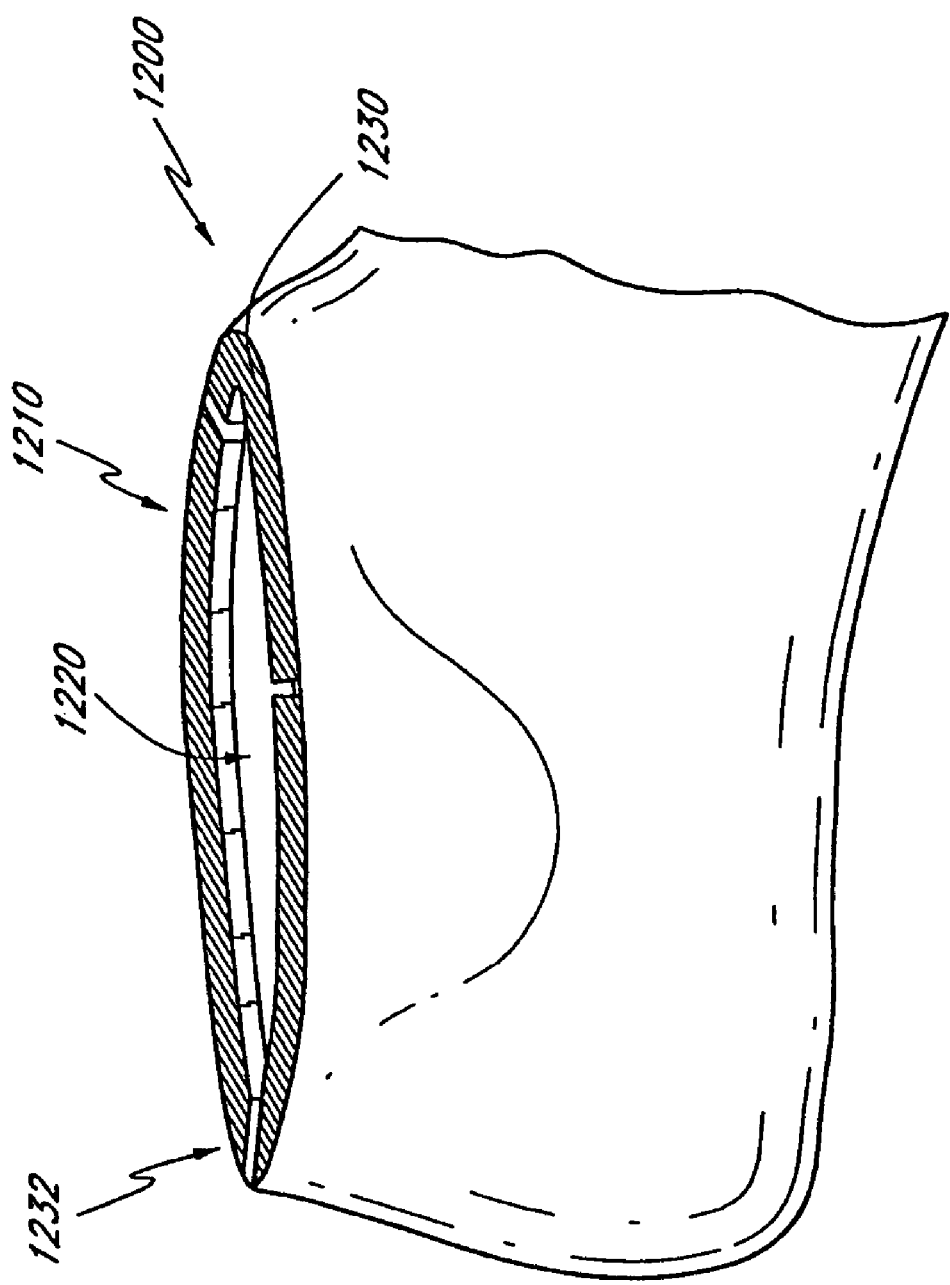
FIG. 11A is a partial side and top view of another embodiment of a functional foot cover.

With reference to FIG. 11A, another embodiment of a functional foot cover 1200 is disclosed. In the illustrated embodiment, the top portion 1210 of the foot cover 1200 proximal an opening 1220 includes a surface of increased area 1230 to facilitate the attachment of foam or other cosmetic filling to the functional foot cover 1200. As shown in FIG. 11, the surface of increased area 1230 includes several slots 1232 to facilitate attachment of the functional foot cover 1200 to foam or other cosmetic filling. One of ordinary skill in the art will recognize that the number of slots 1232 on said foot cover 1200 can vary so as to be fewer or more than those depicted in FIG. 11A.

Figure 11B:
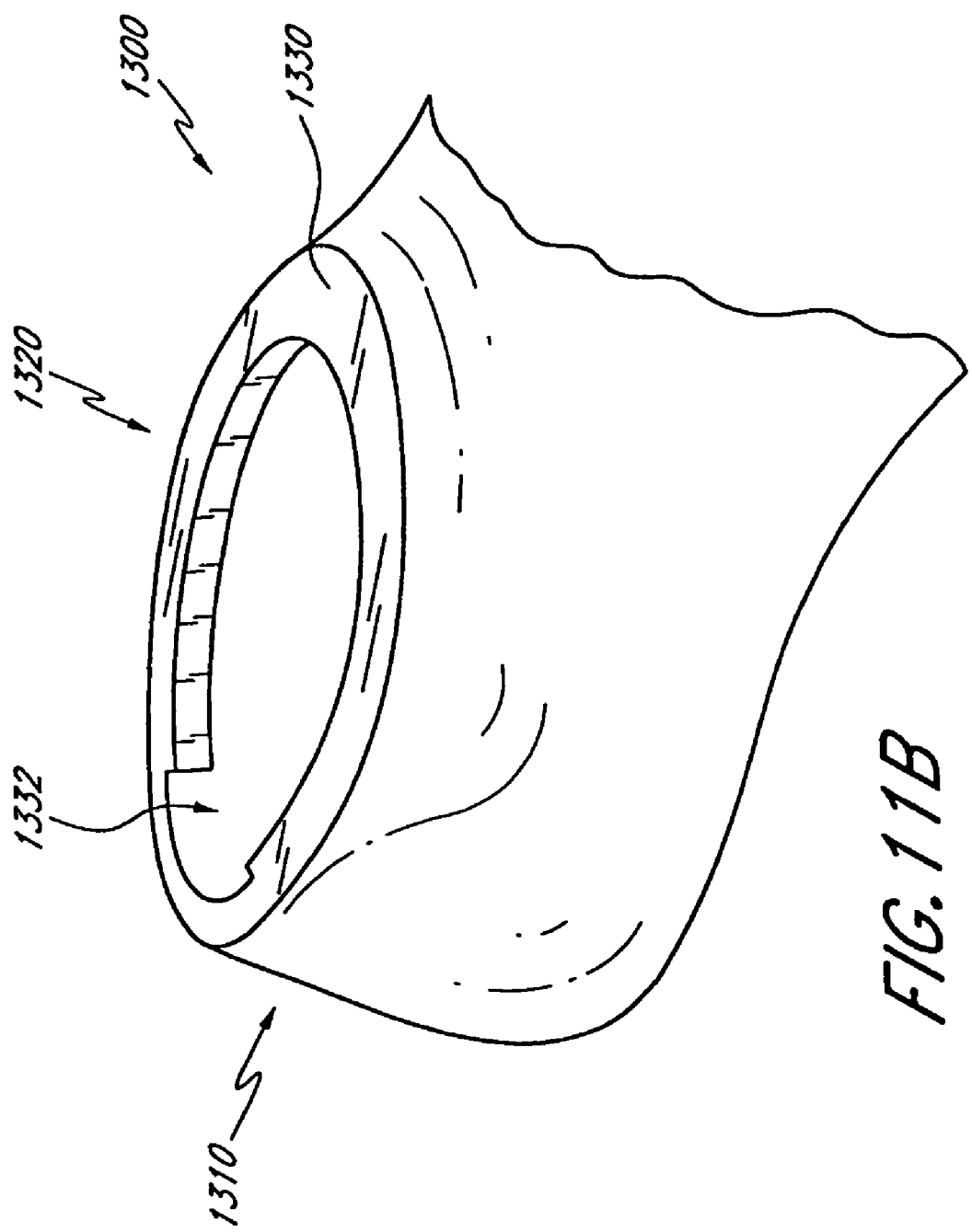
FIG. 11B is a partial side and top view of another embodiment of a functional foot cover.

FIG. 11B illustrates another embodiment of a functional foot cover 1300 having a surface of increased area 1330 on a top portion 1320 of the foot cover 1300. In the illustrated embodiment, the surface of increased area 1330 defines a recess 1332 proximal a heel section 1310 of the foot cover 1300. Said recess 1332 is preferably sized so as to facilitate attachment of the foot cover 1300 to foam or other cosmetic filling.

Figure 12:
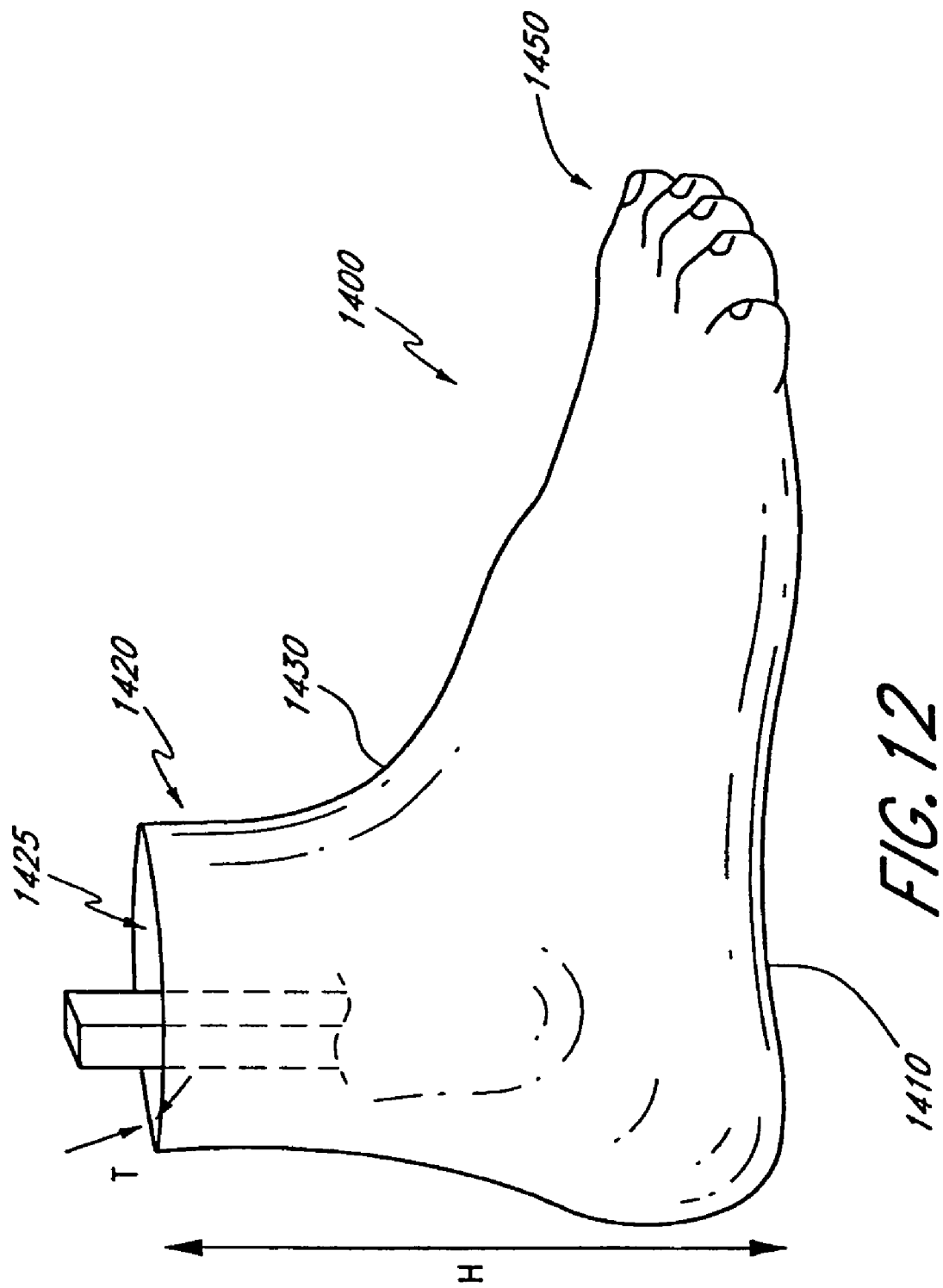
FIG. 12 is a top and side profile view of another embodiment of a functional foot cover.

FIG. 12 illustrates another embodiment of a functional foot cover 1400. In the illustrated embodiment, a height H of the foot cover 1400 is generally higher than conventional foot covers. For example, the height H of the foot cover 1400 can be between about 7 cm and about 10 cm. In other embodiments, the height H of the foot cover 1400 can be greater than about 10 cm. Preferably, a wall 1430 of the foot cover 1400 has a thickness T that tapers from a thicker section at the bottom 1410 of the foot cover 1400 toward a thinner section proximal an opening 1425 at a top end 1420 of the foot cover 1400. In another embodiment, the wall 1430 of the foot cover 1400 has a stepped thickness T, with a thicker section proximal the bottom 1410 of the foot cover 1400 and a thinner section proximal the top end 1420 of the foot cover 1400. Preferably, the thickness T of the wall 1430 at the opening 1425 of the foot cover 1400 is between about ¼ and about ½ the thickness T of the wall 1425 proximal the bottom 1410 of the foot cover 1400. In other embodiments, the thickness T of the wall 1430 at the opening 1425 of the foot cover 1400 can be between about ⅛ and about ¾ of the thickness T of the wall 1430 proximal the bottom 1410 of the foot cover 1400. Said tapered thickness T advantageously facilitates the insertion of a prosthetic device within the foot cover 1400.

Figure 13A:
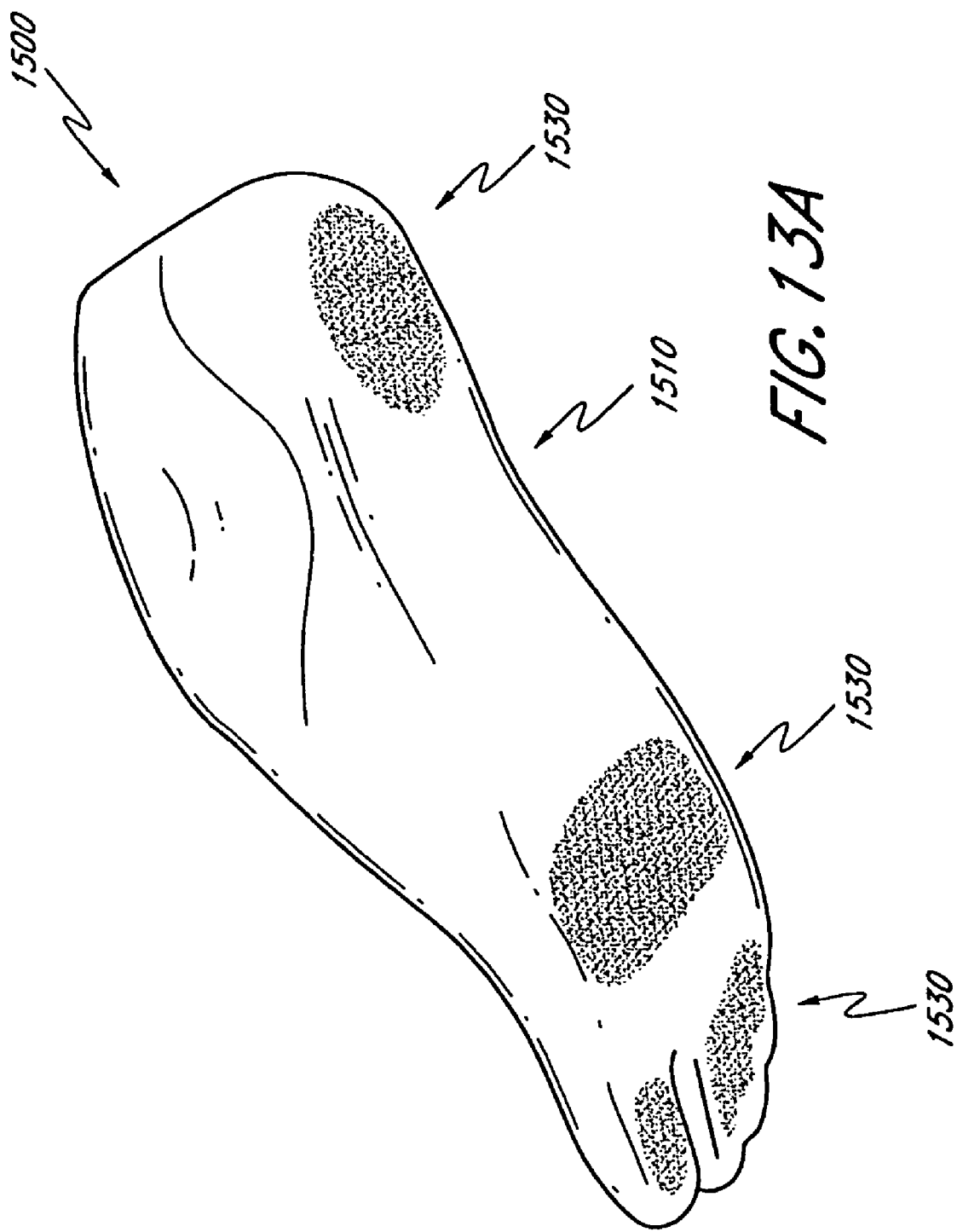
FIG. 13A is a partial bottom and side profile view of another embodiment of a functional foot cover.
Figure 13B:
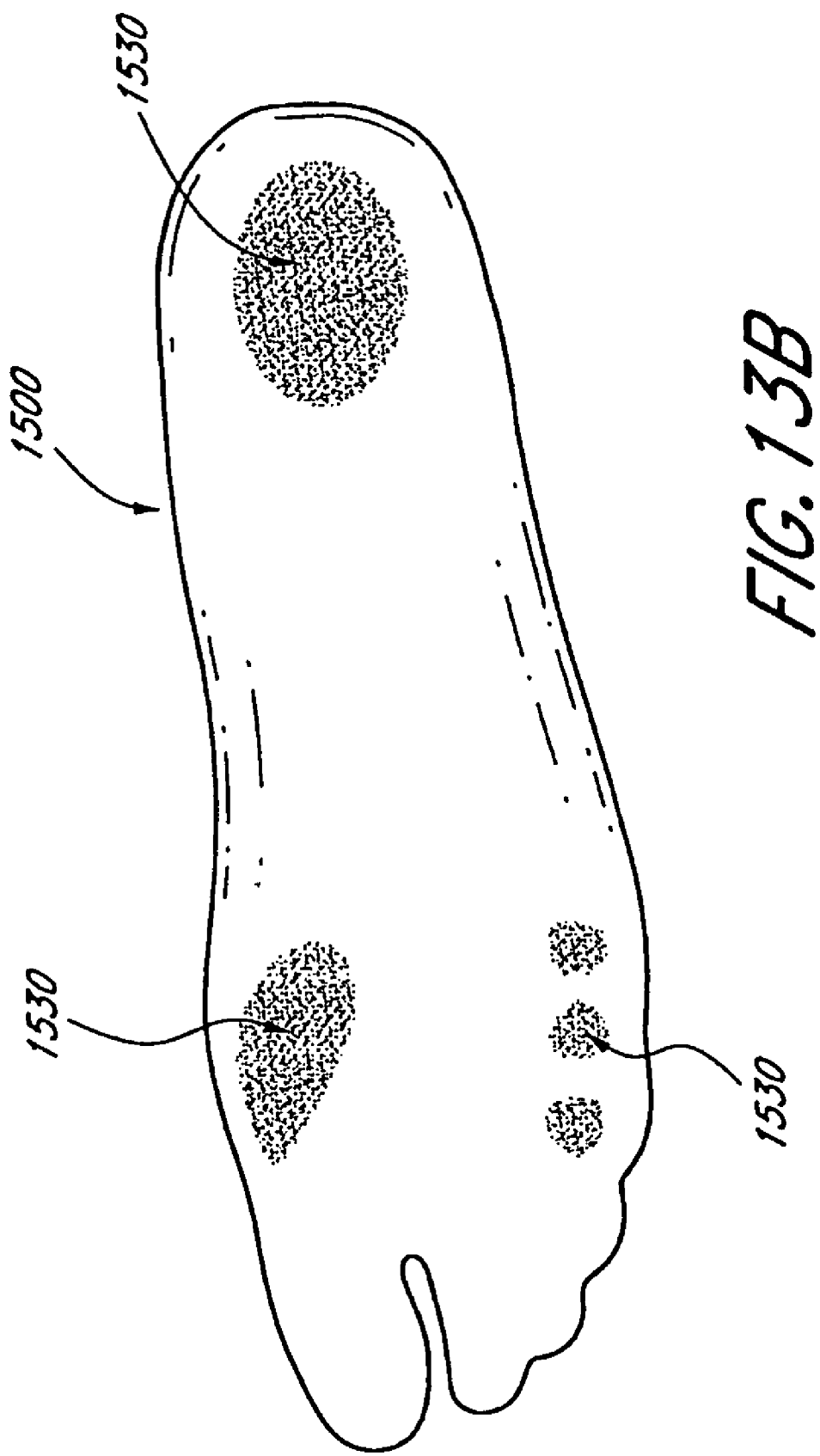
FIG. 13B is a partial bottom plan view of the functional foot cover in FIG. 13A.

FIGS. 13A and 13B illustrate another embodiment of a functional foot cover 1500. In the illustrated embodiment, a sole 1510 of the foot cover 1500 includes areas of non-slip material 1530. Preferably, said areas of non-slip material 1530 increase the traction of the foot cover 1500 during slippery conditions, such as on a wet surface. In one embodiment, said areas of non-slip material 1530 include a pattern designed to increase traction of the foot cover 1500 during use. Preferably, the areas of non-slip material 1530 are molded to the sole 1510 of the foot cover 1530 during manufacture. In another embodiment, the areas of non-slip material 1530 can be applied to the bottom 1510 of the functional foot cover 1500. For example, the non-slip material 1530 can be sprayed onto the bottom 1510 of the foot cover 1500. In a preferred embodiment, the non-slip material 1530 comprises silicone. However, other materials having suitable non-slip characteristics can be used. In one embodiment, the non-slip material 1530 is applied to substantially the entire sole 1510 of the foot cover 1530. In another embodiment, the non-slip material 1530 is applied to selected localized areas on the sole 1510 of the foot cover 1500.

With respect to any of the embodiments described above, the functional foot cover can be manufactured to resemble a human foot, both male and female, and have five toes. In one embodiment, the foot cover can be used with a sandal. For example, as illustrated in FIG. 5, among other figures, the foot cover 500 can have a slot 550 between at least two of the toes 552, 554 formed on the foot cover 500, said slot 550 configured to receive a strap of a sandal. In another embodiment, the foot cover defines several toes disposed adjacent each other without any intervening slots therebetween.

Additionally, any of the embodiments discussed above can be manufactured so as to closely resemble the person's foot. In one embodiment, a person's foot is scanned and a mold of said foot manufactured based on said scanning. Preferably, foot covers of varying sizes are manufactured using said foot scan. Advantageously, construction of a foot cover using a mold based on a scanned foot provides a more accurate anatomical representation of a natural human foot.

Of course, the foregoing description is that of certain features, aspects and advantages of the present invention to which various changes and modifications can be made without departing from the spirit and scope of the present invention. Moreover, the functional foot cover may not feature all objects and advantages discussed above to use certain features, aspects and advantages of the present invention. Thus, for example, those skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still following the scope of the invention. Accordingly, it should be understood that various features and aspects of the disclosed embodiments can be combined with or substituted for one another in order to form varying modes of the discussed functional foot cover.

What is claimed is:

1. A cosmesis cover for a foot prosthesis, comprising:
   an opening at a top end of the cosmesis cover extending into a cavity formed within the cosmesis cover, the cavity configured to receive a prosthesis therein; and
   a wall surrounding the cavity and defining a cosmesis body configured to removably receive a prosthetic foot therein, the wall comprising:
      an upper portion formed as a single piece body with a sole portion, the sole portion having a toe section, a heel section, and a metatarsal region; and
      an inner surface and an outer surface, the outer surface having the shape and contours of a natural human foot such that the cosmesis body has the appearance of a natural human foot;
   wherein the sole portion is provided with varying levels of stiffness, the medial side of the sole portion in the metatarsal region having a different stiffness than the lateral side of the sole portion in the metatarsal region, said difference in stiffness in the metatarsal region selected to cause rollover of the foot prosthesis toward the medial side of the cosmesis cover during ambulation.

2. The cover of claim 1, wherein the varying levels of stiffness are provided by materials of different stiffness disposed in recesses formed in the sole portion.

3. The cover of claim 2, wherein the recesses are formed on the outer surface of the cover.

4. The cover of claim 1, wherein the varying levels of stiffness are provided by materials of different stiffness embedded in the sole portion of the cover.

5. The cover of claim 1, wherein the varying levels of stiffness are provided by three materials of selected stiffness disposed along the sole portion.

6. The cover of claim 5, wherein one material of selected stiffness is disposed at the heel section, a second material of selected stiffness is disposed on at least a portion of the metatarsal region, and a third material of selected stiffness is disposed along the toe section.

7. The cover of claim 1, wherein the sole portion is a unitary single piece body.

8. The cover of claim 1, wherein the sole portion is a continuous solid surface.

9. The cover of claim 1, wherein the outer surface of the sole portion has the shape and contours of a sole portion of a natural human foot.

10. A cosmesis cover for a foot prosthesis, comprising:
    an opening at a top end of the cosmesis cover extending into a cavity within the cosmesis cover, configured to receive a prosthesis therein; and
    a wall surrounding the cavity and defining a cosmesis body configured to removably receive a prosthetic foot therein, the wall comprising:
       an upper portion formed as a single piece body with a sole portion, the sole portion having a toe section, a heel section, and a metatarsal region; and
       an inner surface and an outer surface, the outer surface having the shape and contours of a natural human foot such that the cosmesis body has the appearance of a natural human foot;
    wherein the sole portion is provided with a plurality of selected regions of differing stiffness relative to regions surrounding said selected regions, a first region on the medial side of the sole portion in the metatarsal region having a lower stiffness than a second region on the lateral side of the sole portion in the metatarsal region.

11. The cover of claim 10, wherein the plurality of selected regions of differing stiffness are configured to guide rollover of the cosmesis body from heel-to-toe in a lateral-to-medial direction.

12. The cover of claim 10, wherein the cover comprises at least three selected regions and at least two of the plurality of selected regions have the same stiffness.

13. The cover of claim 10, wherein the stiffness of one of the plurality of selected regions is lower than the stiffness of the region surrounding said selected region.

14. The cover of claim 10, wherein the stiffness of one of the plurality of selected regions is higher than the stiffness of the region surrounding said selected region.

15. The cover of claim 10, wherein the selected regions of differing stiffness are provided as inserts disposed in the outer surface of the cover.

16. The cover of claim 10, wherein the selected regions of differing stiffness are provided as materials of different stiffness embedded in the sole portion of the cover.

17. The cover of claim 10, wherein the plurality of selected regions of differing stiffness include regions at the heel section and the metatarsal region.

18. The cover of claim 10, wherein the sole portion is a unitary single piece body and wherein the selected regions of differing stiffness are embedded in the sole portion such that the selected regions of differing stiffness are seamless with regions surrounding said selected regions of differing stiffness.

19. The cover of claim 10, wherein the selected regions of differing stiffness are embedded in the sole portion such that the selected regions of differing stiffness are seamless with regions surrounding said selected regions of differing stiffness.

20. The cover of claim 10, wherein the outer surface of the sole portion has the shape and contours of a sole portion of a natural human foot.

21. A cosmesis cover for a foot prosthesis, comprising:
an opening at a top end of the cosmesis cover extending into a cavity within the cosmesis cover, configured to receive a prosthesis therein; and
a wall surrounding the cavity and defining a cosmesis body configured to removably receive a prosthetic foot therein, the wall comprising:
an upper portion formed as a single piece body with a sole portion, the sole portion having a toe section, a heel section, and a metatarsal region; and
an inner surface and an outer surface, the outer surface having the shape and contours of a natural human foot such that the cosmesis body has the appearance of a natural human foot;
wherein the sole portion is provided with at least a first selected region of reduced stiffness relative to a region surrounding said selected region, the first selected region disposed at the medial side of the sole portion in the metatarsal region, the reduced stiffness selected to cause the rollover of the prosthetic foot toward the medial side of the cosmesis cover during ambulation.

22. The cover of claim 21, wherein a second selected region of reduced stiffness is disposed at the heel section.

23. The cover of claim 21, wherein the sole portion is a unitary single piece body and wherein the first selected region of reduced stiffness is embedded in the sole portion such that the first selected region of reduced stiffness is seamless with regions surrounding said first selected region of reduced stiffness.

24. The cover of claim 21, wherein the first selected region of reduced stiffness is embedded in the sole portion such that the first selected region of reduced stiffness is seamless with regions surrounding said first selected region of reduced stiffness.

25. The cover of claim 21, wherein the outer surface of the sole portion has the shape and contours of a sole portion of a natural human foot.

26. In combination, a prosthetic foot having a plate-like carbon-filament foot plate and a cosmesis cover that removably covers the prosthetic foot, the cosmesis cover comprising a cosmesis body having an upper portion and a sole portion, the upper portion and sole portion being a single piece, an outer surface of the cosmesis body on the upper and sole portions and extending between a rear end and a front end of the cosmesis body having the shape and contours of a natural human foot such that the cosmesis body has the appearance of a natural human foot, the sole portion having a toe section, a heel section, and a metatarsal region, the cosmesis body having an opening at a top end of the cosmesis body that extends into a cavity formed within the cosmesis body, the cavity configured to removably receive the prosthetic foot therein, wherein the metatarsal region of the sole portion has varying levels of stiffness, the medial side of the sole portion in the metatarsal region having a different stiffness than the lateral side of the sole portion in the metatarsal region, said difference in stiffness in the metatarsal region selected to cause rollover of the foot prosthesis toward the medial side of the cosmesis cover during ambulation of the prosthetic foot.

27. The combination of claim 26, wherein the varying levels of stiffness are provided by sections of different stiffness in the sole portion of the cover.

28. The combination of claim 26, wherein a bottom surface of the foot plate is in contact with an inner surface of the cosmesis body along substantially the entire length of the foot plate.

* * * * *